(12) United States Patent
Sandoz et al.

(10) Patent No.: US 12,163,111 B2
(45) Date of Patent: Dec. 10, 2024

(54) CELL CULTURE DEVICE

(71) Applicant: PHILIP MORRIS PRODUCTS S.A., Neuchatel (CH)

(72) Inventors: Antonin Sandoz, Neuchatel (CH); David Bovard, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 539 days.

(21) Appl. No.: 16/955,192

(22) PCT Filed: Dec. 19, 2018

(86) PCT No.: PCT/EP2018/085943
§ 371 (c)(1),
(2) Date: Jun. 18, 2020

(87) PCT Pub. No.: WO2019/121984
PCT Pub. Date: Jun. 27, 2019

(65) Prior Publication Data
US 2020/0318048 A1  Oct. 8, 2020

(30) Foreign Application Priority Data
Dec. 20, 2017  (EP) .................................... 17208965

(51) Int. Cl.
*C12M 1/32* (2006.01)
*C12M 1/00* (2006.01)
(Continued)

(52) U.S. Cl.
CPC ............ *C12M 23/12* (2013.01); *C12M 23/00* (2013.01); *C12M 25/04* (2013.01); *C12N 5/0062* (2013.01)

(58) Field of Classification Search
CPC ...... C12M 23/12; C12M 23/00; C12M 25/04; C12N 5/0062
(Continued)

(56) References Cited

U.S. PATENT DOCUMENTS

| 8,808,687 B2 | 8/2014 | Humayun | |
|---|---|---|---|
| 2003/0129654 A1* | 7/2003 | Ravkin | G01N 33/54313 435/7.1 |
| 2008/0125020 A1* | 5/2008 | Jiang | B24B 37/26 451/527 |

(Continued)

FOREIGN PATENT DOCUMENTS

| CN | 103351484 | 10/2013 |
|---|---|---|
| EP | 0552412 | * 7/1993 |

(Continued)

OTHER PUBLICATIONS

Liu, M. et al. "Self-Assembling Halloysite Nanotubes into Concentric Ring Patterns in a Sphere-on-Flat Geometry." Langmuir. 33, 3088-3098. 2017. (Year: 2017).*

(Continued)

*Primary Examiner* — Jill A Warden
*Assistant Examiner* — Jacqueline Brazin
(74) *Attorney, Agent, or Firm* — Mueting Raasch Group

(57) ABSTRACT

There is described a method of reducing or preventing the agglomeration of spheroids comprising the use of a cell culture device comprising: a cell culture chamber comprising a base and side walls extending from the base to enclose a volume of the cell culture chamber; an inlet in the base or side walls of the cell culture chamber adapted for fluid communication into the chamber; and an outlet in the base or side walls of the cell culture chamber adapted for fluid communication out of the chamber; wherein the base of the cell culture chamber comprises a discontinuous surface adapted to reduce or prevent the agglomeration of spheroids.

12 Claims, 12 Drawing Sheets

(51) Int. Cl.
  *C12M 1/12* (2006.01)
  *C12N 5/00* (2006.01)
(58) Field of Classification Search
  USPC .......................................................... 435/325
  See application file for complete search history.

(56) References Cited

U.S. PATENT DOCUMENTS

| | | | | |
|---|---|---|---|---|
| 2009/0018033 | A1* | 1/2009 | Morgan | C12M 25/00 435/375 |
| 2010/0112690 | A1* | 5/2010 | Eddington | C12M 29/06 435/297.5 |
| 2011/0195489 | A1* | 8/2011 | Lan | C12M 33/02 435/283.1 |
| 2013/0022500 | A1* | 1/2013 | Angeloni Suter | C12M 23/00 29/559 |
| 2014/0322806 | A1* | 10/2014 | Bennett | C12M 29/04 435/325 |
| 2016/0097028 | A1* | 4/2016 | Tung | C12M 23/16 435/29 |
| 2017/0342363 | A1 | 11/2017 | Fang | |
| 2018/0251721 | A1 | 9/2018 | Hashimoto | |

FOREIGN PATENT DOCUMENTS

| | | | | |
|---|---|---|---|---|
| JP | 2010-000020 | | 1/2010 | |
| JP | 2010088347 | | 4/2010 | |
| JP | 2017-012109 | | 1/2017 | |
| JP | 2017-532974 | | 11/2017 | |
| JP | 2017-217530 | | 12/2017 | |
| JP | 2018-102285 | | 7/2018 | |
| KR | 20130044809 | * | 5/2013 | |
| WO | WO 95/24464 | | 9/1995 | |
| WO | WO-2006089354 A1 | * | 8/2006 | ............ C12M 21/06 |
| WO | WO 2008/121417 | | 10/2008 | |
| WO | WO-2014173832 A1 | * | 10/2014 | ........... C12N 5/0656 |
| WO | WO 2016/069892 | | 5/2016 | |
| WO | WO-2016069895 A1 | * | 5/2016 | ............ C12M 21/08 |

OTHER PUBLICATIONS

PCT Search Report and Written Opinion for PCT/EP2018/085943 dated Feb. 26, 2019 (11 pages).
European Extended Search Report for Application No. 17208965.8 dated Jun. 13, 2018 (6 pages).
Database WPI Week 201028, Thomson Scientific, London, GB, AN 2010-E36690, XP002781639 & JP 2010 088347 (NIPRO), Apr. 22, 2020, abstract, Fig. 2.
Office Action issued in Singapore for Application No. 11202005559V dated Dec. 16, 2021 (7 pages).
Office Action issued in Japan for Application No. 2020-533291 dated Nov. 22, 2022 (8 pages). English translation included.
Office Action issued in China for Application No. 201880081064.5 dated Aug. 24, 2023 (9 pages). English translation included.

* cited by examiner

Units = mm

Units = mm

Units = mm

Units = mm

Units = mm

Units = mm

Units = mm

Units = mm

Units = mm

Well 1

| Well Diameter [mm] | Well height [mm] | Viscosity [dynes/cm2] | Flow [ml/min] |
|---|---|---|---|
| 11 | 3 | 0.00653 | 200 |

Shear Stress = 0.08

Well 2

| Well Diameter [mm] | Well height [mm] | Viscosity [dynes/cm2] | Flow [ml/min] |
|---|---|---|---|
| 16 | 3.5 | 0.00653 | 200 |

Shear Stress = 0.04

(a)

(b)

CELL CULTURE DEVICE

This application is a U.S. National Stage Application of International Application No. PCT/EP2018/085943 filed Dec. 19, 2018, which was published in English on Jun. 27, 2019 as International Publication No. WO 2019/121984 A1. International Application No. PCT/EP2018/085943 claims priority to European Application No. 17208965.8 filed Dec. 20, 2017.

FIELD OF THE INVENTION

The present invention relates to cell culture devices, methods and uses thereof. One particular cell culture type for use in the present disclosure is 3D organotypic cells or tissues, also known as spheroids.

BACKGROUND TO THE INVENTION

Toxicological studies using 2-dimensional cell culture systems have been used to examine the effects of one or more agents (for example, drugs) on cell survival and enzyme activity etc. While being able to grow cells in flat layers on plastic surfaces is straightforward and permits the study of several aspects of cellular physiology and responses to stimuli, such cell cultures do not reflect the real structure and architecture of an organ. In 2-dimensional monolayers, the extracellular matrix, the cell-to-cell and cell-to-matrix interactions, which are essential for the differentiation, proliferation and cellular functions, are lost.

3-dimensional culture systems can form a functional tissue with similar features to those observed in vivo. As compared to the 2-dimensional culture systems, 3-dimensional cell culture allows cells to interact with their surroundings in all three dimensions and is more physiologically relevant. Such cell cultures can show improvements in viability, proliferation, differentiation, morphology, response to stimuli, drug metabolism, gene expression and protein synthesis and the like. 3-dimensional cell culture can produce specific tissue-like structures and mimic functions and responses of real tissues in a manner that is more physiologically relevant than traditional 2-dimensional cell monolayers.

Different techniques have been developed for 2-dimensional and 3-dimensional cell culture. 3-dimensional cell culture methods include the use of hanging drop plates, magnetic levitation, or biomaterial scaffolds.

In one spheroid preparation method, cells are seeded into wells where they are allowed to agglomerate at the bottom of the well. Once the cells form an agglomerate, they will form a single or multiple spheroids in each well. From here, the spheroids can be used for any required purpose—such as in experiments that evaluate the spheroids, which may include their viability, their morphology or their functionality and the like.

The present invention seeks to provide improvements relating to 3-dimensional cell culture.

SUMMARY OF THE INVENTION

The present inventors have been studying 3-dimensional cell culture. Unexpectedly, they observed that spheroids can have a tendency to agglomerate or fuse together in the same place during 3-dimensional cell culture to form a single large tissue. This can be problematic because when spheroids fuse together they form a bigger tissue. This means that it is almost impossible to determine exactly the number of spheroids present in this bigger tissue which means that the tissue cannot be used for other experiments in which it is important to know the precise number of spheroids. Without wishing to be bound by theory, the inventors have observed that cells in the middle of a spheroid have less access to nutrients compared to cells located towards the outside of the spheroid, such that cells towards the middle of the spheroid have a tendency to die. This becomes very problematic when spheroids agglomerate (which can occur after 5 hours of cell culture) because a higher number of cells in the spheroid will have less access to nutrients. This also further increases the number of dead cells within the spheroid. This can be problematic for a number of reasons, including: (1) molecules released from the dead cells can have a negative impact on other cells in the spheroid; (2) dead cells are not metabolically active, so the metabolic activity of the spheroid will be reduced; and (3) many assays require the use of a single spheroid or a known number of spheroids. The present inventors' sought to solve the problem of spheroids agglomerating in 3-dimensional cell culture. They surprisingly discovered that this problem can be elegantly solved by forming a discontinuous surface on the base of a cell culture chamber—such as a well of a multi-well plate—so that spheroids on the discontinuous surface in the chamber become trapped in the discontinuous surface. This effectively reduces the extent of or prevents the agglomeration or fusion of the spheroids. Advantageously, the inventors' discovered that spheroids can be maintained as individualised single spheroids in accordance with the present disclosure.

In one aspect of the present invention, there is disclosed a method of reducing or preventing the agglomeration of spheroids comprising the use of a cell culture device comprising: a cell culture chamber comprising a base and side walls extending from the base to enclose a volume of the cell culture chamber; an inlet in the base or side walls of the cell culture chamber adapted for fluid communication into the chamber; and an outlet in the base or side walls of the cell culture chamber adapted for fluid communication out of the chamber; wherein the base of the cell culture chamber comprises a discontinuous surface adapted to reduce or prevent the agglomeration of spheroids.

In one embodiment of the present invention, the method comprises (i) providing one or more individual spheroids; (ii) transferring the individual spheroid(s) into the cell culture chamber of the cell culture device; (iii) incubating the individual spheroid(s) in the cell culture device; and (iv) obtaining an individual spheroid(s) on the discontinuous surface of the cell culture device.

In one embodiment of the present invention, a known number of individual spheroids are transferred in step (ii) and a known number of individual spheroids are obtained in step (iv).

In one embodiment of the present invention, the discontinuous surface comprises a plurality of grooves in which the depth and width of the grooves is between about 200 to about 1000 μm, flow suitably, between about 200 to about 600 μm.

In one embodiment of the present invention, the grooves form a plurality of concentric rings on the base of the cell culture chamber.

In one embodiment of the present invention, the discontinuous surface comprises a plurality of holes having a closed bottom and an open top, the size of the holes corresponding in depth and width to be about 10% greater than the largest diameter of a spheroid.

In one embodiment of the present invention, the cell culture chamber is manufactured from PEEK.

In one embodiment of the present invention, the cell culture chamber is coated, suitably, wherein the coating is a coating of poly(p-xylylene) polymer.

In one embodiment of the present invention, between about 40 to about 100 spheroids are transferred to the cell culture chamber of the cell culture device.

In one embodiment of the present invention, a medium flow is applied to the cell culture chamber of the cell culture device, suitably, wherein the flow rate is between about 10 to about 1000 µL/min.

In another aspect of the present invention, there is disclosed the use of a cell culture device for reducing or preventing the agglomeration of spheroids, said cell culture device comprising: a cell culture chamber comprising a base and side walls extending from the base to enclose a volume of the cell culture chamber, an inlet in the base or side walls of the cell culture chamber adapted for fluid communication into the chamber; and an outlet in the base or side walls of the cell culture chamber adapted for fluid communication out of the chamber; wherein the base of the cell culture chamber comprises a discontinuous surface adapted to reduce or prevent the agglomeration of spheroids.

In another aspect of the present invention, there is disclosed a multi-well cell culture plate wherein at least one of the wells of the multi-well cell culture plate and/or an insert contained in at least one of the wells of the multi-well cell culture plate comprises a discontinuous surface adapted to reduce or prevent the agglomeration of spheroids.

In another aspect of the present invention, there is disclosed an insert for use in a multi-well cell culture plate comprising a discontinuous surface adapted to reduce or prevent the agglomeration of spheroids.

In one embodiment, the plate and/or insert is manufactured from PEEK.

In one embodiment, at least one of the wells and/or the insert is coated, suitably, wherein the coating is a coating of poly(p-xylylene) polymer.

In one embodiment, the at least one well and/or insert comprises an individualised single spheroid.

In one embodiment, the base of the cell culture chamber is substantially circular in shape In one embodiment, the diameter of the base is between about 6 mm±5% and about 22 mm±5%, suitably, wherein the diameter of the base is about 6 mm±5%, about 11 mm±5%, about 16 mm±5% or about 22 mm±5%.

In one embodiment, the discontinuous surface comprises a plurality of grooves in which the depth and width of the grooves corresponds to the largest diameter±10% of a spheroid.

In one embodiment, the depth and width of the plurality of grooves is between about 200 to about 1000 µm, suitably, between about 600 to about 1000 µm.

In one embodiment, the grooves form a plurality of concentric rings on the base of the cell culture chamber.

In one embodiment, the discontinuous surface comprises a plurality of holes having a closed bottom and an open top, the size of the holes corresponding in depth and width to be about 10% greater than the largest diameter of a spheroid.

In one embodiment, the cell culture chamber comprises cell culture medium for culturing spheroids.

In one embodiment, the cell culture chamber comprises individual spheroids trapped in the discontinuous surface of the cell culture chamber.

In one embodiment, the spheroids are lung spheroids.

In one embodiment, the flow of fluid from the inlet to the outlet of the cell culture chamber, when fluid is present therein, is between about 10 to about 1000 µL/min, suitably, about 1 to about 500 µL/min, suitably, about 40 µL/min.

In one embodiment, the shear stress in the cell culture chamber is less than about 0.1 dynes/cm$^2$—such as about 0.08 dynes/cm$^2$ or less or about 0.04 dynes/cm$^2$ In one embodiment, the cell culture device is a multi-well plate and each chamber of the multi-well plate is a well, said multi-well plate comprising at least two wells.

In one embodiment, the base of at least one of the chambers comprises a flat surface that is devoid of discontinuities.

In one embodiment, the at least one chamber comprises an insert positioned above the base of the chamber, suitably, wherein the insert is located on top of a permeable membrane located inside the chamber to form a surface that is capable of culturing a cell at an air/liquid interface.

In one embodiment, the depth of the at least one chamber comprising the flat surface that is devoid of discontinuities is different to the depth of the at least one chamber comprising the discontinuous surface, suitably, wherein the depth of the at least one chamber comprising the flat surface that is devoid of discontinuities is less than the depth of the at least one chamber comprising the discontinuous surface.

In one embodiment, the cell culture chamber comprises cell culture medium for culturing a cell at an air-liquid interface.

In one embodiment, the cell culture chamber comprises cells positioned on the permeable membrane, said cells being capable of growing at an air-liquid interface.

In one embodiment, the cells are lung cells.

In one embodiment, the at least two wells are in fluid communication with each other.

Suitably, the discontinuous surface is as defined herein.

Suitably, the discontinuous surface is provided to the base using computer numerical control machining or injection moulding.

Suitably, the device is a multi-well plate.

Suitably, the chamber is a well.

DETAILED DESCRIPTION

Figure 1:
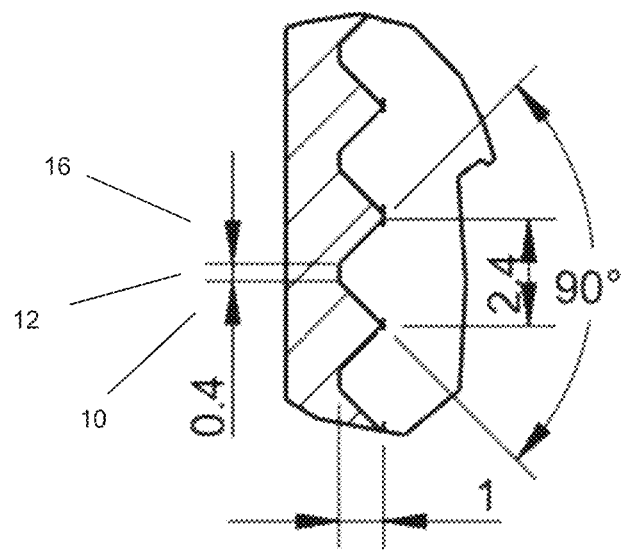
FIG. 1 is a cross-section of the well with a plurality of concentric grooves for trapping individual spheroids (marked as 'see detail B' in FIG. 4). Dimensions are in millimetres.

The practice of the present disclosure employs, unless otherwise indicated, conventional techniques of engineering, micro-engineering, microbiology, cell biology and biochemistry. Such techniques are explained fully in the literature, such as, in Molecular Cloning: A Laboratory Manual, second edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. CelMs, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, I B. Griffiths, and D. G. Newell, eds., 1993-8) J. Wiley and Sons; Methods in Enzymology (Academic Press, Inc.); Current Protocols in Molecular Biology (F. M. Ausubel et al., eds., 1987); PCR: The Polymerase Chain Reaction, (Mullis et al., eds., 1994). Procedures employing commercially available kits and reagents will typically be used according to manufacturer-defined protocols unless otherwise indicated.

The technical terms and expressions used herein are generally to be given the meaning commonly applied to them in the pertinent art of molecular biology, microbiology, cell biology and biochemistry. All of the following term definitions apply to the complete content of this application.

As used herein, the singular forms "a", "an", and "the" include both singular and plural referents unless the context clearly dictates otherwise.

The term "and/or" means (a) or (b) or both (a) and (b).

The terms "comprising", "comprises" and "comprised of" as used herein are synonymous with "including", "includes" or "containing", "contains", and are inclusive or open-ended and do not exclude additional, non-recited members, elements or method steps.

The term "consisting of" means that additional components are excluded and has the recited elements only and no more.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Cell Culture

Cell culture generally refers to the removal of cells from a tissue prior to growth in an artificial environment. The cells to be cultured can be removed directly from a tissue containing the cell to be cultured and optionally treated with enzymatic or mechanical means prior to culture. As an alternative, the cells to be cultured can be derived from a prior established strain or line of cell.

In vitro culturing of cells provides material necessary for studying various aspects of a cell including the physiology; the biochemistry; the effects of agents, including aerosols; the screening and development or optimisation of agents; the study of agent efficacy; the study of agent absorption; toxicity screenings; toxicology; target discovery; pharmacokinetics; pharmacodynamics; and regenerative medicine, optionally in real-time.

Cells are typically grown in a cell culture device comprising a chamber or container. Examples of such cell culture devices include bottles, dishes and plates—such as microtiter plates, or multi-well plates or microplates, flasks—such as common flasks and multi-layered cell growth flasks, vessels and bioreactors. Cells in culture will typically attach to and grow on the bottom of the container immersed in a suitable cell culture or sustaining media. The chamber or container will include ports for directing the flow of cell culture media into and out of the chamber or container.

The cell culture device of the present disclosure includes a cell culture chamber comprising a base and side walls extending from the base to enclose a volume of the cell culture chamber. The ports for directing the flow of cell culture media into and out of the chamber can include: (1) an inlet in the base or side walls of the cell culture chamber that is adapted for fluid communication into the chamber and; (2) an outlet in the base or side walls of the cell culture chamber adapted for fluid communication out of the chamber. The cell culture chamber comprises a discontinuous surface adapted to reduce or prevent the agglomeration of spheroids, as described below. Suitably, the inlet and the outlet are located above the discontinuous surface.

Cell Culture Device

In one embodiment, the cell culture device is a multi-well plate in the form of a flat plate comprising at least two chambers in the form of wells (for example, a plurality or numerous wells). In general, the whole plate is rectangular and the well capacity can be from several μL to several mL, as required.

In at least one of the at least two wells, the base of the well comprises a discontinuous surface adapted to reduce or prevent the agglomeration of spheroids.

The multi-well plate can be manufactured in various formats—such as in 24- or 48- or 96- or 384- or 1536-well/chamber formats—and can be readily selected by the skilled person based upon the size and choice of the experiment that it is intended to be carried out. The multi-well plate can be a standard plate that is commercially available and very well known to the skilled person.

Suitably, when the chamber is in the form of a well, the base thereof is substantially circular in shape.

Suitably, the diameter of the base is between about 6 mm±5% and about 22 mm±5%, suitably, wherein the diameter of the base is about 6 mm±5%, about 11 mm±5%, about 16 mm±5% or about 22 mm±5%.

The multi-well plate can be configured to contain at least two sequentially arranged wells.

The multi-well plate can be configured to contain at least two linearly arranged wells.

The wells in a multi-well plate are arranged in rows. For example, an 8-well plate can be configured in 2 linear rows of 4 adjacent wells in each row. By way of further example, a 24-well plate can be configured in 4 linear rows of 6 adjacent wells in each row. By way of further example, a 48-well plate can be configured in 6 linear rows of 8 adjacent wells in each row. By way of further example, a 96-well plate can be configured in 8 linear rows of 12 adjacent wells in each row. Multi-well plates can even be manufactured or custom-built, if required, to provide the desired number of wells in the plate.

The cell culture device can be fitted with a lid on top of the device which helps to reduce the evaporation of cell culture medium and risk of contamination. The lid is preferably not sealed so that air can circulate inside the device which can assist in the culturing/maintenance of cells.

The composition of the cell culture device is not particularly limited provided that it is not cytotoxic and is suitable for cell culture. It can be manufactured from an acrylic resin, a polyglycolic acid, a styrene type resin, a polylactic acid, an acrylic or styrene type copolymer resin, a polycarbonate resin, a polyvinyl alcohol-based resin, a polyester-based resin, an ethylene or vinyl alcohol copolymer resin, a vinyl chloride resin, a thermoplastic elastomer, a silicone resin, or any combination thereof. It can be made from polytetrafluoroethylene (PTFE), stainless steel (for example, 316 L/1.4435), polyether ether ketone (PEEK), polypropylene or polysulfone or a combination of one or more thereof. A coating—such as a coating of poly(p-xylylene) polymers or poly-2-hema—can be applied, if required.

In certain embodiments, the use of PEEK is especially preferred as it has the advantage of not being absorbent towards small molecules—such as nicotine and NNK, as described below.

The cell culture device can be designed by computer-aided design (CAD) if required or, if the cell culture device is based on a standard multi-well plate, then the standard multi-well plate will be commercially available. CAD plates can be produced by micro-mechanical machining using methods that are well known in the art.

The cell culture device—such as the multi-well plate—contains an inlet in the base or side walls of the cell culture chamber adapted for fluid communication into the chamber and an outlet in the base or side walls of the cell culture chamber adapted for fluid communication out of the chamber, optionally into an adjacent well. This allows for the flow of fluid—such as culture medium—over the spheroids and their exposure to fluid flow. In certain embodiments, this can be achieved by, for example, forming at least one hole in one or more of the wells of the cell culture plate and then connecting one or more of the wells via the hole(s) to a channel (for example, a conduit or pipe). In one embodiment, the channel(s) are directly machined or embedded inside the cell culture plate to provide for the connection of the at least two wells. Suitably, the channel(s) run under the cell culture chamber. The channel can contain openings at each end. The channel can be a microfluidic channel. Typically, at least one end of the opening is connected to a pump. Each end of the opening can terminate in the same pump or a different pump.

Various kinds of connectors can be used to connect the channel to a first pump. One example is a Luer connector—such as a Luer-lock connector—or a simple tube connector.

The channel can be configured to join together in fluid communication a first row of wells and a second row of wells and optionally a third row of wells and so on, as required. The channel can be configured as a U-bend to connect the different rows of wells. The U-bend can be located internally or externally of the cell culture device. When the loop is located externally of the cell culture device then a connector—such as a Luer connector or Luer-lock connector or a simple tube connector—can be used to seal and engage the U-bend to the cell culture device.

Tubing can be used to connect the different channels together—such as silicon tubing or PharMed® tubing.

When fluid is carried in the channel, it can be carried from the pump and then returned back to the pump, if required. The fluid can be circulated in a clockwise or anti-clockwise fashion through the wells as required. More than one pump can be used, if required.

In certain embodiments, the flow of fluid from the inlet to the outlet of the cell culture chamber, when fluid is present therein, is between about 10 to about 1000 μL/min, suitably, about 1 to about 500 μL/min, suitably, about 10 to about 500 μL/min, suitably, about 40 μL/min, or suitably, about 1 to about 60 μL/min. As will be appreciated by the skilled person, when fluid flows over a solid boundary it will incur a shear stress on that boundary, which may lead to the perturbation of cells exposed to the shear stress. In the context of the present disclosure, when fluid moves through the cell culture device, a shear stress will be created. It is desirable that the shear stress in the cell culture chamber is less than about 0.1 dynes/cm$^2$—such as about as 0.08 dynes/cm$^2$ or less or 0.04 dynes/cm$^2$ or less—as this does not cause perturbation of cells exposed to the shear stress. The shear stress can be different in different types of cell culture chamber. For example, a cell culture chamber with a discontinuous surface can have a shear stress of about 0.04 dynes/cm$^2$. For example, a cell culture chamber with a flat and non-discontinuous surface can have a shear stress of about 0.08 dynes/cm$^2$. Suitably, the shear stress in the cell culture chamber with a discontinuous surface is lower than a cell culture chamber with a flat and non-discontinuous surface.

So that optical analysis can be used for screening, the bottom of the chamber or the container or the well can be made of a material having a total light transmittance of 70% or 80% or 90% or more.

In one embodiment, the cell culture device uses a microfluidic cell culture plate which is widely available in the art. For example, a M04S microfluidic cell culture plate is available from Cellasic, California, USA, and contains 4 independent wells/chambers, each well/chamber is 2.8 mm in diameter with a 120 micron height.

In one aspect, the cell culture device of the present disclosure is in the form of a multi-well cell culture plate. At least one of the wells of the multi-well cell culture plate can comprise a discontinuous surface adapted to reduce or prevent the agglomeration of spheroids. As will be appreciated by the skilled person, a cell culture device—such as a multi-well cell culture plate—can comprise various component parts that can be fitted together to form the complete cell culture device. In use, not all of these component parts have to be present in the device. Thus, for example, certain cells for use in the present disclosure can be optionally cultured in inserts which can be housed in the wells of a cell culture plate, as desired herein below. Thus, in a further aspect, there is also described an insert for use in a cell culture device—such as a multi-well cell culture plate—comprising a discontinuous surface adapted to reduce or prevent the agglomeration of spheroids. The cell culture device and/or the insert can manufactured from PEEK as described in detail herein. The cell culture device and/or the insert can be coated as described in detail herein, suitably, wherein the coating is a coating of poly(p-xylylene) polymer. The cell culture device and/or the insert can comprise an individualised single spheroid as described in detail herein.

Pump

One or more pump(s) for use in the present disclosure can be a positive displacement pump that is operable to circulate fluid—such as a peristaltic pump. As understood in the art, a peristaltic pump is a pump used for moving a fluid. The fluid can be contained within a channel described herein—the channel can be a flexible tube that fits inside a pump casing. In the alternative, if the channel is directly machined (for example, embedded) into the plate then an adaptor can be used to connect the machined or embedded channel to the pump. A rotor attached to the external circumference thereof compresses the flexible tube or channel. As the rotor turns, the part of the tube or channel under compression is pinched closed to force the fluid through the tube or channel.

In one embodiment, the pump(s) comprise a stepper motor or a brushless motor comprising an encoder.

Each motor can be controlled by a motor controller, the operation and the sensors of which can be controlled by a microcontroller.

Inserts

Certain cells for use in the present disclosure can be cultured in inserts which can be housed in the wells of the cell culture device, as desired. Cells are typically grown on a permeable membrane contained in the insert. In general, the cells will be grown on top of the permeable membrane. The insert is placed in a well or chamber. When the well or chamber is filled with fluid—such as cell culture medium—the fluid will pass through the permeable membrane and contact the cells so that they can be cultured in the insert. Different types of cells can be cultured in the insert as described herein. Inserts are commercially available. By way of example, ThinCert™ permeable cell culture inserts (USA Scientific, Florida, USA) can be used. These are available in various sizes and finishes and can be readily selected by the skilled person for use in the present disclosure. Each insert can have self-positioning hangers that eliminate capillary effects and maximize pipettor access by positioning the insert slightly off-centre. ThinCert™ cell culture inserts are compatible with standard multiwell plates. By way of further example, Corning® HTS Transwell®-permeable supports (Sigma Aldrich, Dorset, United Kingdom) can be used. Corning® HTS Transwell®-permeable supports have an array of 24 or 96 wells with permeable inserts connected by a rigid tray. As described herein, there is disclosed an insert for use in a multi-well cell culture plate comprising a discontinuous surface adapted to reduce or prevent the agglomeration of spheroids.

Discontinuous Surface

According to the present disclosure, the base of the cell culture chamber—such as the base of a well in a multi-well plate—or the insert comprises a discontinuous surface adapted to reduce or prevent the agglomeration of spheroids. It is to be understood that not every chamber or well or insert that may be contained in the cell culture device needs to include the discontinuous surface as not all chambers or wells may be used for the culture of spheroids and an insert may not be present in every well. For example, some wells may be used for the culture of other cell types, which do not require the use of the discontinuous surface or an insert. For example, some wells may be used for the culture of other cell types, which require or do not require the use of an insert to create an air-liquid interface.

Suitably, the discontinuous surface traps the spheroids to reduce or prevent the agglomeration or fusion thereof. Suitably, the discontinuous surface traps single spheroids to reduce or prevent the agglomeration or fusion thereof.

In certain embodiments, the discontinuous surface is formed by one or more grooves. The grooves can function to trap the spheroids to reduce or prevent the agglomeration thereof. The size of the groove(s) will generally correspond to the largest diameter±10% of a spheroid so that the spheroids can be trapped or held in the groove(s). Suitably, the groove(s) will cover the majority of the base of the cell culture chamber or the insert as the presence of a flat surface on the base of the cell culture chamber or the insert can lead to the spheroids agglomerating, which can lead to the formation of large cell aggregates which is not desirable. In certain embodiments, at least 70%, 80%, 90%, 95%, 99% or 100% of the base of the cell culture chamber or the insert will contain the discontinuous surface—such as the groove(s).

Suitably, the depth and width of the discontinuous surface—such as the plurality of grooves—in the base of the cell culture chamber or the insert is between about 200 µm to about 1000 µm, suitably, between about 200 µm to about 600 µm. A depth and width of about 600 µm to about 1000 µm is also disclosed. The actual depth and width will be determined by the size of the spheroids which are intended to be used in the cell culture chamber or the insert and trapped. So, for example, some spheroids have a maximum diameter of about 600 µm, in which case the depth and width of the discontinuous surface—such as the plurality of grooves—will be about 600 µm±10%. In some embodiments, it is desirable for the depth and width of the discontinuous surface—such as the plurality of grooves—to be greater than the maximum diameter of the spheroid—such as 20%, 30%, 40%, 50% or 60% or more greater than the maximum diameter of the spheroid. In one embodiment, the spheroid has a maximum diameter of 600 µm and the discontinuous surface—such as the plurality of grooves has a height of about 1 mm and a width of about 1 mm or a width of about 2 mm.

Generally, the shape of the grooves can be a flat shaped bottom, a U-shape, a V-shape, or a V-shape with a flat bottom and the like. In one embodiment, the grooves have a V-shape with a flat bottom. In one embodiment, the maximum width of the opening of the groove is about 2.4 mm, the depth of the groove is about 1 mm and the width of the flat bottom on the base of the groove is about 400 µm. The angle of the opposing sides of the groove according to this embodiment is about 90 degrees.

Turning to FIG. 1, there is shown a cell culture device 10 comprising a cell culture chamber 12 with a plurality of grooves 16 on the base thereof containing V-shaped grooves each with a flat bottom. The maximum width of the opening in the grooves is about 2.4 mm, the depth of the grooves is about 1 mm and the width of the flat bottom on the base of the grooves is about 400 μm. The angle of the opposing sides of the grooves is about 90 degrees. Although the plurality of grooves are illustrated as having the same shape it is contemplated that grooves with different shapes can be used. For example, the base of the cell culture chamber or the insert may comprise a plurality of grooves in which the shape of one or more of the grooves is different. The base of the cell culture chamber or the insert may therefore comprise a plurality of grooves containing two or more of a flat shaped bottom, a U-shape, a V-shape, or a V-shape with a flat bottom and the like.

Figure 2:
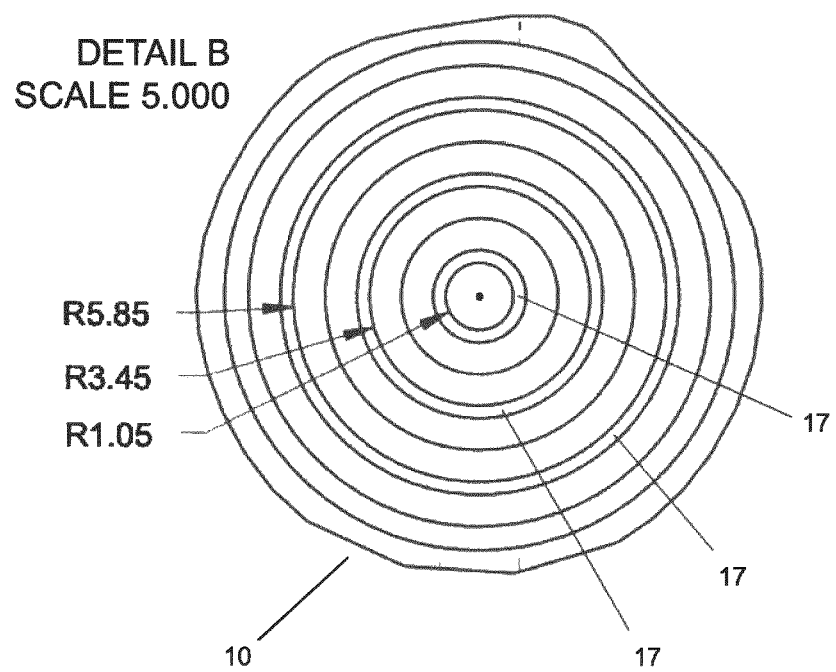
FIG. 2 is a plan view of the well with a plurality of concentric grooves for trapping individual spheroids (marked as 'see detail B' in FIG. 4). Dimensions are in millimetres.
Figure 3:
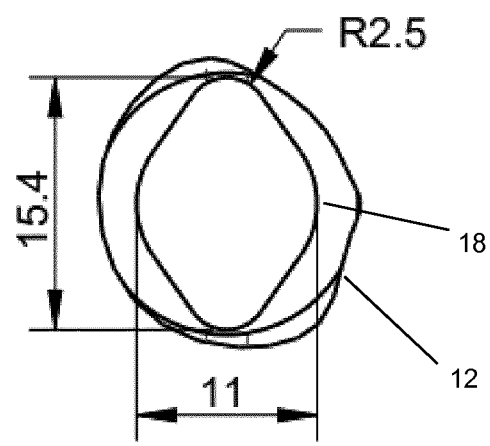
FIG. 3 is a plan view of the well containing a microfluidic channel (marked as 'see detail C' in FIG. 4). Dimensions are in millimetres.

In certain embodiments, the grooves form a plurality of concentric rings on the base of the cell culture chamber or the insert. In one embodiment, the radius of the concentric rings is about 1.05 mm, about 3.45 and about 5.85 mm. Turning to FIG. 2, there is shown the base of a cell culture chamber 12 with a plurality of concentric rings 17 formed by the grooves 16, the radius of the concentric rings being about 1.05 mm, about 3.45 and about 5.85 mm.

Figure 4:
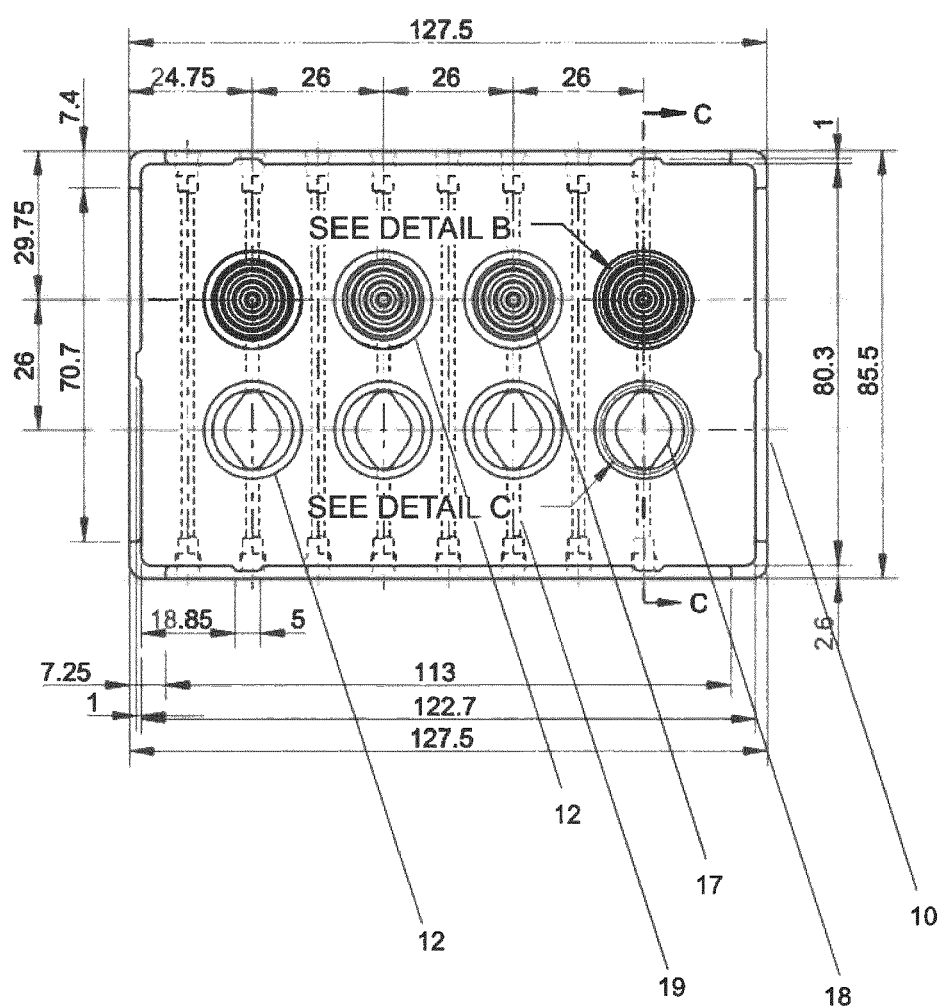
FIG. 4 is a plan view of a multi-well plate containing wells with a plurality of concentric grooves for trapping individual spheroids (marked as 'see detail B') and wells containing an insert (marked as 'see detail C'). The wells are connected by a channel such that each of the first well (see detail B') and the second well (see detail C') are in fluid communication with each other. Dimensions are in millimetres.

Turning now to FIG. 4, there is shown a plan view of a cell culture device 10 in the form of a multi-well plate. The cell culture device 10 contains a plurality of cell culture chambers 12 in the form of wells, the wells containing either a plurality of concentric grooves 17 or containing a microfluidic channel 18. The wells are arranged linearly in rows. A row can be configured to contain at least one well containing the concentric grooves 17. A row can be configured to contain at least one well containing the concentric grooves 17 and at least one well containing a microfluidic channel 18, as shown in FIG. 4.

A channel 19 connects a well containing a plurality of concentric grooves 17 and a well containing a microfluidic channel 18. Each well contains an inlet and an outlet for fluid communication into each well and out of each well. Although FIG. 4 shows every cell culture chamber 12 in the cell culture device 10 containing either the concentric grooves 17 or containing the microfluidic channel 18, the skilled person will understand that it is not essential for every cell culture chamber 12 to be configured in this way and that is possible for one or more of the cell culture chambers 12 to not contain the concentric grooves 17 and/or to not contain the microfluidic channel 18. Some of the cell culture chambers 12 can be empty and not used, as required.

In certain embodiments, the discontinuous surface is formed by one or more grooves that are shaped as waves across the base of the cell culture chamber or the insert.

In certain embodiments, the discontinuous surface comprises a plurality of holes. The holes will typically have a closed bottom and an open top. The holes function to trap individual spheroids to reduce or prevent the agglomeration thereof. The size of the holes will generally correspond to the largest diameter±10% of a spheroid so that the spheroids can be trapped or held in the holes. The discontinuous surface may contain 10, 20, 30, 40, 50, 60, 70, 80, 90, 100, 110, 120, 130, 140, 150, 160, 170, 180, 190 or 200 or more holes distributed across the bottom of the cell culture chamber. The discontinuous surface may contain from 130 to 160 holes distributed across the bottom of the cell culture chamber. The discontinuous surface may contain from 130 to 150 holes distributed across the bottom of the cell culture chamber. The discontinuous surface may contain from 130 to 140 holes distributed across the bottom of the cell culture chamber or the insert. Generally, the shape of the holes can include a flat shaped bottom, a U-shape, a V-shape, or a V-shape with a flat bottom and the like. The shape of the holes is not particularly limited provided that the holes are able to accommodate the largest diameter±10% of a spheroid in order to trap individual spheroids. In certain embodiments, the depth and width of the holes is between about 200 to about 1000 um, suitably, between about 600 to about 1000 μm. In certain embodiments, at least 70%, 80% or 90% or more of the base of the cell culture chamber or the insert will be populated with holes.

Figure 6:
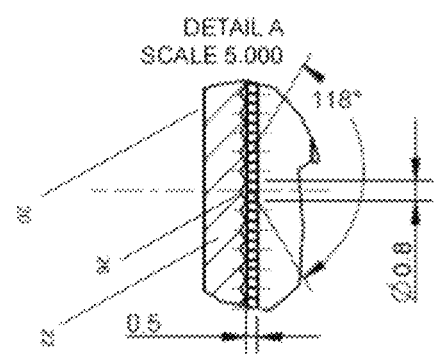
FIG. 6 is a cross-section of the well with a plurality of holes on the base thereof to achieve the function of trapping individual spheroids (marked as 'see detail B' in FIG. 8).

Turning to FIG. 6, there is shown a cell culture device 20 comprising a cell culture chamber (well) 22 with a plurality of holes 26 on the base thereof. The holes have a closed bottom and an open top. The maximum width of each hole is about 0.8 mm, the depth of the grooves is about 0.5 mm. The angle of the opposing sides of the holes is about 118 degrees. Although the plurality of holes are illustrated as having the same shape it is contemplated that holes with different shapes can be used. For example, the base of the cell culture chamber or the insert may comprise a plurality of holes in which the shape of one or more of the holes is different. The base of the cell culture chamber or the insert may therefore comprise a plurality of holes containing two or more of a flat shaped bottom, a U-shape, a V-shape, or a V-shape with a flat bottom and the like.

Figure 7:
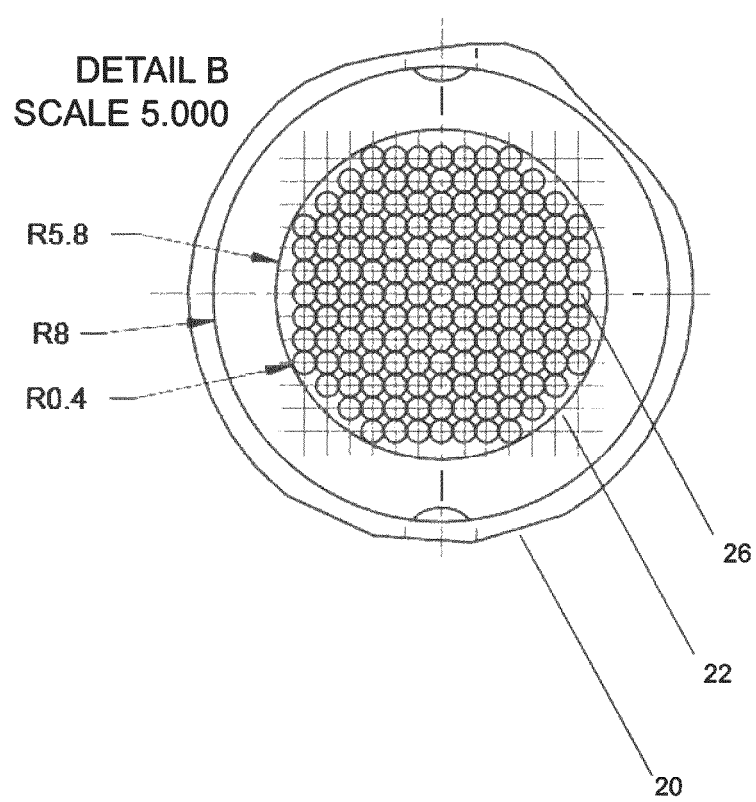
FIG. 7 is a plan view of a well with a plurality of holes for trapping individual spheroids on the base thereof, as shown in FIG. 6. Dimensions are in millimetres.

FIG. 7 illustrates a plan view of the cell culture device 20 shown in FIG. 6. The radius of the cell culture chamber 22 is about 8 mm. The radius of the base of the chamber 22 containing the plurality of holes 26 is about 5.8 mm. The radius of each hole 26 is about 0.4 mm.

Figure 8:
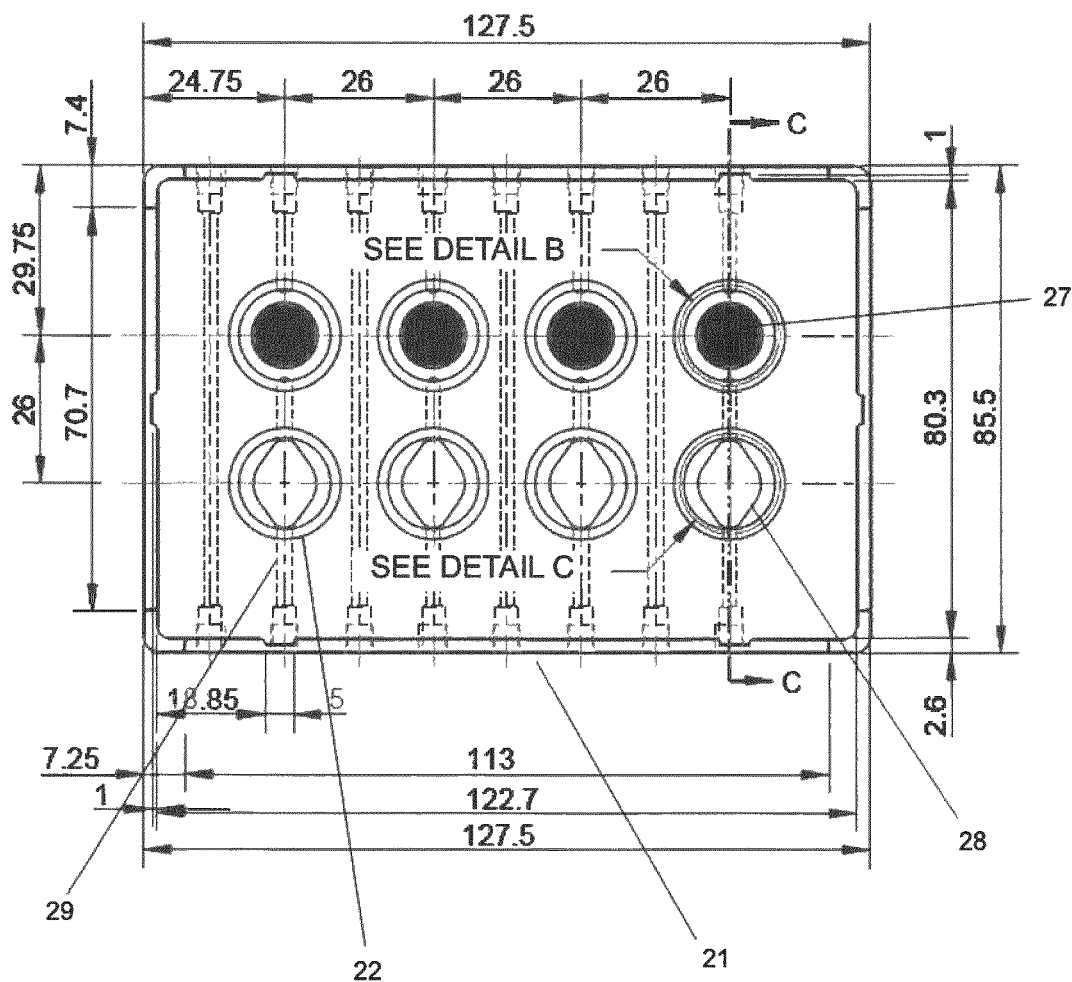
FIG. 8 is a plan view of a multi-well plate containing wells with a plurality of holes for trapping individual spheroids (marked as 'see detail B') and wells containing an insert (marked as 'see detail C'). The wells are connected by a channel such that each of the first well (see detail B') and the second well (see detail C') are in fluid communication with each other. Dimensions are in millimetres.

Turning now to FIG. 8, there is shown a plan view of a cell culture device 20 in the form of a multi-well plate. The cell culture device 21 contains a plurality of cell culture chambers 22 in the form of wells, the wells containing either a plurality of holes 27 or containing a microfluidic channel 28. The wells 22 are arranged linearly in rows. A row can be configured to contain at least one well containing the plurality of holes 27. A row can be configured to contain at least one well containing the plurality of holes 27 and at least one well containing a microfluidic channel 28. A channel 29 connects a well containing a plurality of holes 27 and a well containing a microfluidic channel 28. Each well contains an inlet and an outlet for fluid communication into each well and out of each well.

Although FIG. 8 shows every cell culture chamber 22 in the cell culture device 21 containing either the holes 27 or containing the microfluidic channel 28, the skilled person will understand that it is not essential for every cell culture chamber 22 to be configured in this way and that is possible for one or more of the cell culture chambers 22 to not contain the holes 27 and/or to not contain the microfluidic channel 28. Some of the cell culture chambers 22 can be empty and not used, as required.

The depth of a plurality of cell culture chambers, when used in accordance with the present disclosure, does not need to be the same across the cell culture device and it is contemplated that cell culture chambers—such as wells of a multi-well plate—can have different depths. In one embodiment, the cell culture chamber comprising the discontinuous surface or the holes has a depth that is greater than the cell culture chamber comprising the insert. The channel connecting the at least two cell culture chambers can be at the same height such that the channel is located at different distances from the base of the at least two cell culture chambers. This configuration ensures that the flow of fluid into the chamber does not perturb or disturb the spheroids trapped on the discontinuous surface, whilst ensuring that the fluid can still pass through the permeable membrane of the insert.

Figure 5:
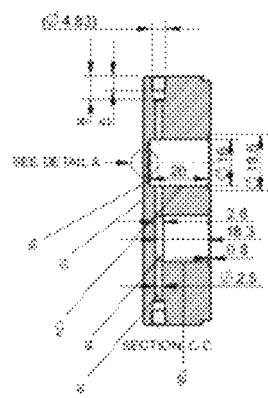
FIG. 5 is a cross sectional view of line C-C in FIG. 4.

This configuration is depicted in FIG. 5, where there is shown a cell culture device 10 comprising a first cell culture chamber 12*a* with a plurality of grooves 16 on the base thereof and a second cell culture chamber 12*b* with a microfluidic channel 18 therein. The first cell culture chamber 12*a* has a depth that is greater than the second cell culture chamber 12*b*. The first cell culture chamber 12*a* has a depth of about 20 mm and the second cell culture chamber 12*b* has a depth of about 18.3 mm. The channel 19 is in fluid communication with each of the cell culture chambers 12*a* and 12*b*. The channel 19 is located further from the base of the first cell culture chamber 12*a* as compared to the second cell culture chamber 12*b*.

Figure 9:
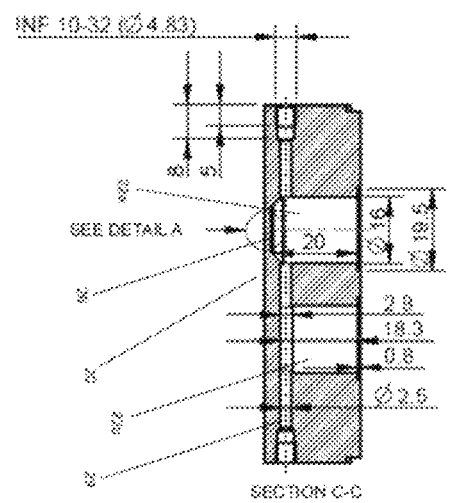
FIG. 9 is a cross sectional view of line C-C in FIG. 8.
Figure 10:
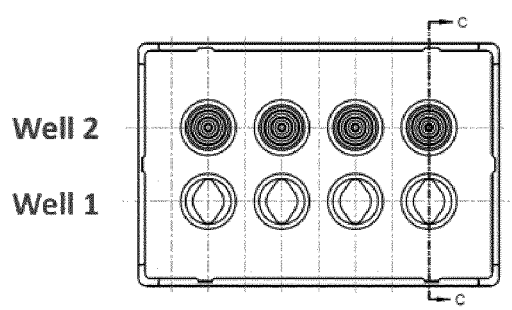
FIG. 10 shows the results of the shear stress calculated for each of the two different wells as shown in the Figure and the parameters used to calculate the shear stress.

A similar configuration is also depicted in FIG. 9, where there is shown a cell culture device 20 comprising a first cell culture chamber 22*a* with a plurality of holes 26 on the base thereof and a second cell culture chamber 22*b* with a microfluidic channel 28 therein. The first cell culture chamber 22*a* has a depth that is greater than the second cell culture chamber 22*b*. The first cell culture chamber 22*a* has a depth of about 20 mm and the second cell culture chamber 12*b* has a depth of about 18.3 mm. The channel 29 is in fluid communication with each of the cell culture chambers 22*a* and 22*b*. The channel 29 is located further from the base of the first cell culture chamber 22*a* as compared to the second cell culture chamber 22*b*.

Spheroids can be used in various experiments to evaluate one or more of their viability, their morphology and their functionality and the like. In such experiments, it can be of importance to make sure that the same number of cells (which also means the same number of spheroids) is used in each experiment. Without the use of a discontinuous surface according to the present disclosure, several spheroids can fuse together to form a bigger tissue. It can be difficult to determine exactly the number of spheroids present in this bigger tissue which means that the tissue cannot be used for other experiments. When the discontinuous surface is used, it increases the distance between the spheroids and reduces or prevents their fusion meaning that they can be used for other experiments as the number of spheroids is known.

Thus, according to one aspect of the present disclosure, there is disclosed a method of reducing or preventing the agglomeration of spheroids comprising the use of a cell culture device comprising: a cell culture chamber comprising a base and side walls extending from the base to enclose a volume of the cell culture chamber; an inlet in the base or side walls of the cell culture chamber adapted for fluid communication into the chamber; and an outlet in the base or side walls of the cell culture chamber adapted for fluid communication out of the chamber; wherein the base of the cell culture chamber comprises a discontinuous surface adapted to reduce or prevent the agglomeration of spheroids.

In one embodiment, the method comprises: (i) providing one or more individual spheroids; (ii) transferring the individual spheroid(s) into the cell culture chamber of the cell culture device; (iii) incubating the individual spheroid(s) in the cell culture device; and (iv) obtaining an individual spheroid(s) on the discontinuous surface of the cell culture device.

The individual spheroids that are provided can be transferred from one entity—such as a well of a cell culture plate. The entity can be separated from the cell culture chamber of the cell culture device into which the individual spheroids are to be transferred. In other words, the entity can be physically separated from the cell culture chamber of the cell culture device. After incubation for a period of time, a single individual spheroid or multiple individual spheroids are present or formed in each well of the multi-well plate. From here, the individual spheroids can be transferred to the cell culture chamber of the cell culture device comprising the discontinuous surface described herein and which is optionally coated. Advantageously, a known number of individual spheroids can be transferred in step (ii) and a known number of individual spheroids can then be obtained in step (iv). In one embodiment, between about 40 to about 100 spheroids are transferred to the cell culture chamber of the cell culture device. The known number of individual spheroids obtained in step (iv) can be incubated for a period of time. The known number of individual spheroids obtained in step (iv) can be subjected to further experimental analysis, as required. In one example of the present disclosure, cells are seeded in each well of a multi-well plate with optional low attachment treatment and an optional U-shaped bottom. Cells are allowed to agglomerate at the bottom of the well. Once the cells form an agglomerate, they will then, for example, within about 3 days, form a spheroid. After incubation, a single spheroid or multiple spheroids are formed in each well of the multi-well plate. The size of the spheroid is determined by the number of cells seeded in each well. From here, the individual spheroids are transferred to the cell culture chamber of the cell culture device comprising the discontinuous surface described herein and which is optionally coated. Each individual spheroid is transferred independently from the multi-well plate to the cell culture chamber of the cell culture device. In one embodiment, about 40 to 100 individual spheroids are transferred to the cell culture chamber of the cell culture device. Finally, the cell culture device is connected to a pump which creates a medium flow. The individual spheroids of known number can stay in this state for between about 1 to about 28 days before being used in other experiments.

Cell Sources

The present disclosure utilises various sources of cells. In one embodiment, the present disclosure excludes the step of isolating or obtaining a cell sample from a subject. The cells can be cryopreserved. The cells can be in 3-dimensional cell culture. The cells can be in the form of tissues. The cells can be in the form of spheroids. The cells can be actively dividing. The cells can be cultured in the cell culture device in the presence of cell culture medium (for example, comprising nutrients (for example, proteins, peptides, amino acids), energy (for example, carbohydrates), essential metals and minerals (for example, calcium, magnesium, iron, phosphates, sulphates), buffering agents (for example, phosphates, acetates), indicators for pH change (for example, phenol red, bromo-cresol purple), selective agents (for example, chemicals, antimicrobial agents), etc.). A single cell culture medium can be used to grow cells of the same or different types. Different cell culture media can be used to grow different types of cells. Since the cell culture media are circulated in accordance with the present disclosure then mixing of the different cell culture media will occur.

In some embodiments, one or more agents are included in the cell culture medium or cell culture media. Cells can be isolated from a tissue or a fluid using methods that are well known in the art. Cells can be differentiated from stem cells—such as embryonic stem cells or induced pluripotent stem cells, or directly differentiated from somatic cells. The cells may be natural cells or altered cells (for example, a cell comprising one or more non-natural genetic alteration). The cell may be a disease cell or disease model cell. For example, the cell can be a cancer cell or a cell that can be induced to a hyper-proliferative state (e.g., transformed cells).

Cells may be or may be derived from human or animal subjects or from human or animal cells, including any of a number of mammalian species, suitably human, but including rat, mouse, pig, rabbit, and non-human primates and the like. Cells and cell lines can be obtained from commercial sources. Cells may be from or derived from any desired tissue or organ type, including but not limited to, adrenal glands, bladder, blood vessel, bone, bone marrow, brain, cartilage, cervix, cornea, endometrium, oesophagus, gastrointestinal system, immune system (e.g., T lymphocytes, B lymphocytes, leukocytes, macrophages, and dendritic cells), liver, lung, lymphatic system, muscle (e.g., cardiac muscle), nervous system, ovaries, pancreas (e.g., islet cells), pituitary gland, prostate, kidney, salivary gland, skin, tendon, testis, and thyroid.

Lung cells—including lung epithelial cells—are one cell type of particular interest. Bronchial and/or other airway epithelial cells are of particular use in the present disclosure. Human bronchial epithelial cells can be collected by brushing donor lungs during a bronchoscopy procedure. In one embodiment, the lung cells are Normal Human Bronchial Epithelial (NHBE) cells. The lung epithelial cells can be cultured as a monolayer of undifferentiated cells or further developed into an organotypic lung epithelium-like tissue at an air-liquid interface. Lung epithelial cells can be obtained from human or animal subjects with different pathologies, including subjects that are classified as smokers or non-smokers.

Liver cells are another cell type of particular interest. In one embodiment, the cells used are hepatocytes. Hepatocytes are cells of the liver, which make up 70-85% of the liver's cytoplasmic mass. The functionality of hepatocytes is highly dependent on their capacity to form a polar phenotype, which is only established in 3-dimensional culture. One source of liver cells is primary hepatocytes which are an in vitro model widely used to investigate numerous aspects of liver physiology and pathology. The technique used to isolate human hepatocytes can be based on a two-step collagenase perfusion of a donated liver. However, these cells do not express metabolic enzymes for more than 5 days. Another limitation is their short viability. These drawbacks can be overcome by the use of alternative, long-lived liver cell lines—such as human or animal hepatic progenitor cell lines. One such example of a human hepatic progenitor cell line is the HepaRG™ cell line (ThermoFisher Scientific). HepaRG™ cells retain many characteristics of primary human hepatocytes. They have greater liver-specific and metabolic gene expression compared to primary hepatocytes and a longer lifespan. Reorganisation of HepaRG™ cells in 3-dimensional spheroids further increases both the lifespan and metabolic capabilities, suggesting that spheroids may provide a better alternative in vitro liver model for toxicity testing. Liver spheroids can also be created with a mixture of primary hepatocytes and liver stellate cells or primary hepatocytes and adipose tissue-derived stem cells.

In one embodiment, the lung cell is a lung epithelial cell—such as a bronchial and/or other airway epithelial cell.

In one embodiment, the liver cell is a hepatocyte, suitably, a HepaRG cell.

Combinations of Cells

The use of combinations of any of the cells described herein is contemplated. The use of combinations of any of the cells described herein in the cell culture device or in a system or device comprising the cell culture device is contemplated. One exemplary combination of cells is the combination of liver and lung cells. The combination of a lung epithelial cell—such as a bronchial and/or other airway epithelial cell, and a liver cell—such as a HepaRG™ cell, is contemplated. Additional cells can be used together with this combination if required. The different cells of the combination can be cultured in separate wells.

3-Dimensional Cell Culture

The present disclosure incorporates the use of "3-dimensional cell culture", which includes any method that provides for the culture of a cell in 3 dimensions, with or without the use of a matrix or scaffold—such as the permeable membrane in the insert. A number of different 3-dimensional cell culture methods have been developed, including spheroid cultures and organotypic cultures. 3-dimensional cells can be grown and/or maintained in the cell culture device described herein.

The term "spheroid" assumes the meaning as normally understood in the art which is either a single cell that divides into a ball of cells in 3-dimensions, or an aggregation of multiple cells in 3-dimensions, either with or without the use of a matrix or scaffold to support 3-dimensional cell growth within the spheroid. The 3-dimensional spheroid can be an adherent spheroid or a spheroid grown in suspension.

In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown.

3-dimensional spheroids more closely resemble in vivo tissue in terms of their cellular communication and development of extracellular matrix. This matrix assists the cells in moving within the spheroid similar to the way cells would move in living tissue. The spheroids are thus much improved models for differentiation, survival, cell migration, cell polarisation, gene expression and growth.

Spheroids can be harvested and studied using various methods well known in the art, including colorimetric, fluorescence, and luminescence assays measured with a plate reader or they can be readily observed by microscopy. Additional techniques include Western, Northern or Southern blot, histological techniques (for example, immunohistochemistry, in situ hybridization, immunofluorescence) and the like. The use of optical imaging methods—such as inverse bright field microscopy and fluorescence microscopy, is also contemplated. Applications of the use of 3-dimensional spheroids include the study of the proliferation of cells and tissues in vitro in an environment that more closely approximates that found in vivo, the screening of compounds, toxicology assays, cell therapy, cell delivery, agent delivery, biochemical replacement, production of biologically active molecules, tissue engineering, biomaterial, and clinical trials and the like.

The use of spheroids in 3-dimensional cell culture is generally reviewed in *Expert Opin. Drug Discov.* (2015) 10, 519-540.

3-dimensional organ culture systems, especially those in miniaturised form, can be used in the present disclosure as they allow the study of how organs function on a microscale. Response to certain stimuli, response to one or more agents, and pharmacokinetic behaviour of such agents can be studied. Miniaturised 3-dimensional cell culture systems allow the combined study of groups of cells or organs. This allows the complexity of interaction between different tissues to be reproduced. The 3-dimensional organ culture can be organotypic, which means that it seeks to reproduce major functions of an organ or organ system. A miniaturised fluidic system interconnecting the wells is also contemplated.

In one aspect, there is provided a culture of spheroids in which the spheroids are in the form of individualised single spheroids after 5 hours of culture or after 5 days of culture. In other words the spheroids are not agglomerated or fused.

Liver Based 3-Dimensional Cultures

The liver plays a central role in detoxification, metabolism of carbohydrates, lipids and proteins as well as biotransformation of endogenous and exogenous substances. Liver functionality is closely linked to the assembly of highly specialised cells, the majority of which are hepatocytes, embedded in a complex 3-dimensional structure made up of so-called lobules. Biotransformation of compounds usually results in non-toxic and more soluble metabolites, however, occasionally, more toxic metabolites may be formed causing hepatotoxicity.

Hepatocytes can be maintained in 3-dimensions via various methods, including the use of sandwich culture, solid scaffold materials—such as polystyrene scaffolds, hydrogels—such as collagen type-I, or self-assemble into spheroids.

Whilst the use of freshly isolated primary human hepatocytes may be the preferred liver cell type, their availability is limited. Other choices of human liver cell lines include HepG2 and Hep2/C3A cells. A particularly suitable cell source is the HepaRG™ cell line. Other sources of human hepatocytes are human embryonic stem cell (hESC)-derived hepatocytes and hepatocytes derived from induced pluripotent stem cells (iPSC).

In one embodiment, the spheroid is or is derived from a liver cell to form a 3-dimensional liver spheroid. Such liver spheroids can be prepared using various methods that are known in the art and described in, for example, *ALTEX* (2014) 31, 441-477 and *Toxicol. Sci.* (2013) 133, 67-78.

Lung Based 3-Dimensional Cultures

As the morphology of the respiratory tract changes from the upper to the lower airways, many different cell culture models have been established using primary airway epithelial cells or cell lines and are contemplated for use in the present disclosure. The choice of exactly which cell or cell line to use will depend on the area of interest of the respiratory tract for a given study.

Since the lung surface is exposed to air, the cell model can be cultured at the air-liquid interface to mimic the lung more realistically.

In one embodiment, the lung 3-dimensional culture is or is derived from a lung cell to form a 3-dimensional organotypic tissue. Such lung tissues can be prepared using various methods that are known in the art, such as those described in *ALTEX* (2014) 31, 441-477 and *Toxicol.* (2013) 133, 67-78.

Screening

The cell culture device of the present disclosure can be used in sampling or screening, optionally, in real-time. The effect of one or more agents on cells contained in the cell culture device can be determined, optionally, in real time. The cell culture device can be used in, for example, agent/drug discovery, agent/drug characterization, efficacy testing, and toxicity testing and the like. It can be used as part of a sampling or screening device. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug/agent interaction assessment, dose assessment, adsorption assessment, disposition assessment, metabolism assessment, elimination studies and the like. Specific cells types may be employed for specific tests (for example, hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity).

In one aspect, there is described an in vitro method for assessing the response of a cell or tissue to an agent, the method comprising: (i) contacting a cell or tissue contained in the cell culture device described herein with at least one agent; and (ii) measuring one or more responses after contact with the at least one agent; wherein a difference in the one or more responses before and after contact with the at least one agent is indicative that the agent modulates the response of the cell or tissue.

In a further aspect, there is described an in vitro method for assessing the response of two or more cells, tissues or organs to an agent, the method comprising: (i) contacting at least one of the cells, tissues or organs contained in the cell culture device as described herein with at least one agent; and (ii) measuring one or more responses in the one or more cells, tissues or organs after contact with the at least one agent; wherein a difference in the one or more responses in the one or more cells before and after contact with the at least one agent is indicative that the agent modulates the response of the at least one cell, tissue or organ. Suitably, the effect or penetration of at least one agent into the cell or tissue is measured or determined. Suitably, the bio-activation of the at least one agent in the cell or tissue is measured or determined. Suitably, the metabolism of at least one agent by the cell or tissue is measured or determined. These steps can be carried out simultaneously or subsequently to each other.

The effect of one or more agents on the penetration of an agent—such as an aerosol—into the one or more cells, tissues or organs and its further bio-activation or metabolism by another cell or tissue can be determined using various methods that are well known in the art.

An agent can be added to the cell culture device and its effect on the cultured cell or tissue contained therein can be monitored or determined. Examples of the effects that can be measured include consumption of oxygen, production of carbon dioxide, cell viability, expression of a protein, the activity of an enzyme, penetration, permeability/barrier function, surfactant production, response to cytokines, transporter function, cytochrome P450 expression, albumin secretion and the like.

The cell culture device can be exposed to an aerosol and its effect on the cultured cell or tissue contained therein can be monitored or determined. Examples of the effects that can be measured include consumption of oxygen, production of carbon dioxide, cell viability, expression of a protein, the activity of an enzyme, penetration, permeability/barrier function, surfactant production, response to cytokines, transporter function, cytochrome P450 expression, albumin secretion and the like.

A plurality of assays may be run in parallel with different concentrations of the agent to obtain a differential response to the various concentrations. As known in the art, the process of determining the effective concentration of an agent typically uses a range of concentrations resulting from 1:10, or other log scale, dilutions. The concentrations may be further refined with a second series of dilutions, if necessary. Typically, one of these concentrations serves as a negative control.

Agent

An agent may be any compound of interest and includes small organic compounds, polypeptides, peptides, higher molecular weight carbohydrates, polynucleotides, fatty acids and lipids, nanoparticles, aerosol or one or more components of an aerosol and the like, a drug, a toxin, a pathogen, an antigen, an antibody, and a small molecule and the like. Agents may be screened individually or in sets or combinatorial libraries of compounds. Agents can be obtained from a wide variety of sources including libraries of synthetic or natural compounds. Libraries of natural compounds in the form of bacterial, fungal, plant and animal extracts can be used. Natural or synthetically produced libraries and compounds that are modified through conventional chemical, physical and biochemical means may be used to produce combinatorial libraries. Known pharmacological agents may be subjected to directed or random chemical modifications, such as acylation, alkylation, esterification, acidification to produce structural analogues for screening. When screening using a combinatorial library, a large library of chemically similar or diverse agents can be screened. In combinatorial screening, the number of hits discovered is proportional to the number of agents tested. A large numbers of compounds, which may reach thousands of compounds tested per day, can be screened, in which laboratory automation and robotics may be applied. Many examples of methods for the synthesis of molecular libraries can be found in the art. A small organic compound includes a compound of molecular weight less than about 5,000 daltons, usually less than about 2,500, usually, less than about 2,000, more usually, less than about 1,500, suitably about 100 to about 1,000 daltons. The small organic compounds may be either biological or synthetic organic compounds. The atoms present in the small organic compound are generally in the group comprising carbon, hydrogen, oxygen, and nitrogen and may include halogens, boron, phosphorus, selenium and sulphur if in a pharmaceutically acceptable form. Generally, oxygen, nitrogen, sulphur or phosphorus, if present, are bound to carbon or one or more of each other or to hydrogen to form various functional groups such as, for example, carboxylic acids, alcohols, thiols, carboxamides, carbamates, carboxylic acid esters, amides, ethers, thioethers, thioesters, phosphates, phosphonates, olefins, ketones, amines, aldehydes, and the like. The small organic compounds, as the term is used herein, also include small peptides, small oligonucleotides, small polysaccharides, fatty acids, lipids, and the like having a molecular weight less than about 5,000 daltons.

Examples of pharmaceutical agents are described in The Pharmacological Basis of Therapeutics, Goodman and Gilman, McGraw-Hill, New York, N.Y., (1996), Ninth edition. The agent can be a toxin.

Agents in solution and solid samples that can be dissolved in a suitable solvent can be assayed. Agents in gaseous form can also be assayed by exposing samples to the gas for a period of time. Samples of interest include environmental samples, biological samples, manufacturing samples, libraries of compounds and synthetic and naturally occurring compounds.

Polypeptides that have a molecular weight of at least about 5,000 daltons, more usually at least about 10,000 daltons can be screened. The test polypeptides will generally be from about 5,000 to about 5,000,000 daltons or more molecular weight, more usually from about 20,000 to about 1,000,000 daltons molecular weight. A wide variety of polypeptides may be considered such as a family of polypeptides having similar structural features, polypeptides having particular biological functions, polypeptides related to specific microorganisms, particularly disease causing microorganisms. Such polypeptides include cytokines or interleukins, enzymes, protamines, histones, albumins, immunoglobulins, scleropolypeptides, phosphopolypeptides, mucopolypeptides, chromopolypeptides, lipopolypeptides, nucleopolypeptides, glycopolypeptides, T-cell receptors, proteoglycans, somatotropin, prolactin, insulin, pepsin, polypeptides found in human plasma, blood clotting factors, blood typing factors, peptide and polypeptide hormones, cancer antigens, tissue specific antigens, nutritional markers, and synthetic peptides, which may or may not be glycated.

Polynucleotides can be screened. The test polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also contemplated. The higher molecular weight polynucleotides can have from about 20 to about 5,000,000 or more nucleotides.

One or more variables that can be measured include quantifiable elements of cells, subcellular material, subcellular components, or cellular products, particularly elements that can be accurately measured in a high throughput assay system or device. An output can be a feature, condition, state or function of any cell, cellular component or cellular product including viability, respiration, metabolism, cell surface determinant, receptor, protein or conformational or posttranslational modification thereof, lipid, carbohydrate, organic or inorganic molecule, DNA, RNA and the like or a portion derived from such a cell component.

While the variable(s) can provide a quantitative readout, in some instances a semi-quantitative or qualitative result can be obtained. Readout variables may include a single value, or a mean value, or a median value or a variance thereof, for example.

Various methods can be used to measure the variable(s) to determine the cell, tissue or organ's response to an agent. For measuring the amount of an agent that is present, one method is to label the agent with a detectable moiety, which may be fluorescent, luminescent, radioactive, enzymatically active, and the like. Fluorescent and luminescent moieties are available for labelling a biomolecule, structure, or cell type. Immunofluorescent moieties can be directed to bind not only to specific proteins but also specific conformations, cleavage products, or site modifications like phosphorylation. Individual peptides and proteins can be engineered to auto-fluoresce. Immunoassay techniques—such as immunohistochemistry, radioimmunoassay (RIA), or enzyme linked immunosorbent assay (ELISA) and related non-enzymatic techniques can be used. These techniques utilize specific antibodies as reporter molecules which are particularly useful due to their high degree of specificity for attaching to a single molecular target. Cell-based ELISA or related non-enzymatic or fluorescence-based methods enable measurement of cell surface parameters.

The results of screening assays may be compared to results obtained from reference compounds, concentration curves, controls and the like. The agent can be an aerosol—such as smoke or an aerosol derived from smoke.

Aerosol

Embodiments of the disclosure can be used for studying the effect of an aerosol on cells, organs or tissues or the penetration of an aerosol into cells, organs or tissues, when contained in the cell culture device of the present disclosure. The aerosol may be derived or generated by an aerosol forming device. Smoking articles and smokable articles are types of aerosol forming devices. Examples of smoking articles or smokable articles include but are not limited to cigarettes, cigarillos, and cigars. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Typically in heated smoking articles, an aerosol is generated by the transfer of heat from a heat source to a physically separate aerosol-forming substrate or material, which may be located within, around or downstream of the heat source. During smoking, volatile compounds are released from the aerosol-forming material by heat transfer from the heat source and entrained in air drawn through the smoking article. As the released compounds cool, they condense to form an aerosol that is inhaled by the user. As used herein, the term 'aerosol forming material' is used to describe a material capable of releasing upon heating volatile compounds, which can form an aerosol. The aerosol forming material may be plant-based. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. The aerosol-forming material may alternatively comprise a non-plant-based-containing material.

The aerosol can be in the form of smoke. As used herein, the term 'smoke' is used to describe a type of aerosol that is produced from combustion, such as from smoking cigarettes, or by combusting an aerosol forming material. Smoke includes various agents, which can be provided as individual compounds for study if required. Examples of such agents include nicotine-free dry particulate matter, carbon monoxide, formaldehyde, acetaldehyde, acetone, acrolein, propionaldehyde, crotonaldehyde, methyl-ethly ketone, butyraldehyde, benzo[a]pyrene, phenol, m-cresol, o-cresol, p-cresol, catechol, resorcinol, hydroquinone, 1,3-butadiene, isoprene, acrylonitrile, benzene, toluene, pyridine, quinoline, styrene, N'-nitrosonornicotine (NNN), N'-nitrosoanatabine (NAT), N'-nitrosoanabasine (NAB), 4-(methylnitrosamino)-1-(3-pyridyl)-1-butanone (NNK), 1-aminonaphthalene, 2-aminonaphthalene, 3-aminobiphenyl, 4-aminobiphenyl, nitrogen oxides (NOx), cyanhydric acid, ammonia, arsenic, cadmium, chrome, lead, nickel, selenium and mercury.

The cell culture device described herein can be exposed for various amounts of time to smoke. Smoke can be delivered using a Vitrocell® Exposure module (see *Chem Cent J.* (2014) 8(1):62). A defined number of puffs per cigarette and a defined number of puffs per minute of exposure can be used and the number of cigarettes varied to adjust to the exposure concentrations. Reference cigarettes—such as the reference cigarettes 3R4F can be used as the source of the smoke and smoked on the smoking robot in basic conformity with the International Organization for Standardization smoking regimen (ISO 2000).

Manufacture

The cell culture device may be made using various manufacturing methods. For example, the device can be assembled using injection moulded parts or manufactured as a single component part. The discontinuous surface can be prepared or applied using computer numerical control machining or injection moulding. Although not required, for optical clarity, it is advantageous to maintain a thickness of no greater than 2 mm. The separate parts may be assembled by various methods including but not limited to: adhesive or solvent bonding, heat sealing or welding, compression, ultrasonic welding, laser welding and/or any other method commonly used for generating seals between parts.

PEEK

As described herein, the cell culture device can be manufactured from PEEK as it has the advantage of not being absorbent towards small molecules. The absorbance of PEEK towards nicotine and NNK, for example, has been tested and it was found that these molecules were not trapped by this material. This can be important since the use of PEEK will not trap small hydrophobic molecules. Therefore, such cell culture devices are particularly suitable for the testing of drug effects on the cells or tissues housed within the device or other such devices without any risk of the drug concentration (or concentration of its metabolites) being altered by the material. Accordingly, there is disclosed a cell culture device or an insert for use in a cell culture device comprising or consisting of PEEK.

Accordingly, there is also disclosed a cell culture device manufactured (exclusively) from PEEK.

There is also disclosed a cell culture plate comprising or consisting of PEEK.

There is also disclosed a cell culture plate manufactured (exclusively) from PEEK.

There is also disclosed a well of a cell culture plate comprising or consisting of PEEK.

There is also disclosed a well of a cell culture plate manufactured (exclusively) from PEEK.

There is also disclosed an insert comprising or consisting of PEEK.

There is also disclosed an insert manufactured (exclusively) from PEEK.

There is also disclosed a multi-well cell culture plate comprising or consisting of PEEK.

There is also disclosed a multi-well cell culture plate manufactured (exclusively) from PEEK. Suitably, the cell culture device, cell culture plate, well or multi-well cell culture plate or insert comprises one or more small hydrophobic molecules—such as one or more small hydrophobic agents. In one embodiment, the agent comprises or consists of a tobacco alkaloid.

In one embodiment, the agent comprises the structure of Formula 1:

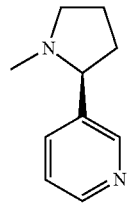

or a pharmaceutically acceptable salt thereof or mixtures thereof;

or, more suitably, the structure of Formula 2:

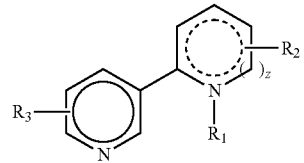

or a pharmaceutically acceptable salt thereof or mixtures thereof;

wherein:

z is 0 or 1;

$R_1$ represents H or $C_1$-$C_7$ alkyl;

$R_2$ represents H, =O, or $C_1$-$C_7$ alkyl;

$R_3$ represents H, halo, or $C_1$-$C_7$ alkyl;

and the dotted line represents either (a) single bonds;

(b) one carbon/carbon or carbon/nitrogen double bond and the remaining single bonds; or (c) two conjugated double bonds independently selected from a carbon/nitrogen double bond and a carbon/carbon double bond and the remaining single bonds.

Suitably, the agent of Formula 2 is:

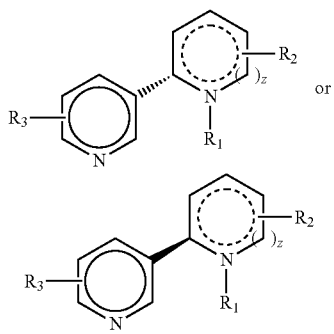

or a pharmaceutically acceptable salt thereof or mixtures thereof.

Suitably, the agent of Formula 2 is:

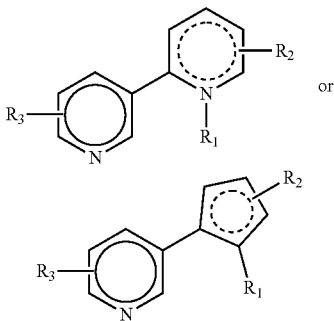

or a pharmaceutically acceptable salt thereof or mixtures thereof.

More suitably, the agent of Formula 1 or Formula 2 is a tobacco alkaloid.

More suitably, the agent of Formula 1 or Formula 2 is nicotine, anabasine, nornicotine, anatabine, cotinine, myosmine or a pharmaceutically acceptable salt thereof or mixtures thereof.

A 'tobacco alkaloid' refers to an alkaloid that is or is derivable from a tobacco plant and can include a synthetic tobacco alkaloid. 'Tobacco plant' refers to a plant belonging to the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setcheffii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. Suitably, the tobacco plant is *N. tabacum*.

'$C_1$-$C_7$ alkyl' refers to straight chain and branched saturated hydrocarbon groups, generally having from 1 to 7 carbon atoms; more suitably $C_1$-$C_6$ alkyl; more suitably $C_1$-$C_3$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like. Suitably, the alkyl group is methyl.

'Halo' refers to F, Cl, Br or I. Suitably, the halo is Cl.

In another embodiment, the agent is a tobacco-specific nitrosamine (TSNA), which is a chemical formed by the nitrosation of secondary and tertiary amines of tobacco alkaloids including nicotine, nornicotine, anatabine, and anabasine. TSNAs are found in some tobacco and tobacco products. Suitably the TSNA is N-nitrosonicotine (NNN), 4-(methylnitrosamino)-1-(3-pyridyl)-1-butanone (NNK), N-nitrosoanabasine (NAB), N-nitrosoanatabine (NAT), 4-(methylnitrosamino)4-(3-pyridyl)butanal (NNA), 4-(methylnitrosamino)-1-(3-pyridyl)-1-butanol (NNAL), 4-(methylnitrosamino)4-(3-pyridyl)-1-butanol (iso-NNAL), or 4-(methylnitrosamino)-4-(3-pyridyl)-1-butyric acid (iso-NNAC), or a pharmaceutically acceptable salt thereof or mixtures thereof. More suitably, the TSNA is 4-(methylnitrosamino)-1-(3-pyridyl)-1-butanone (NNK) or a pharmaceutically acceptable salt thereof.

Suitably, the organic solvent is selected from saturated aliphatic hydrocarbons (e.g., n-pentane, n-hexane, n-heptane, n-octane); aromatic hydrocarbons (e.g., benzene, toluene, xylenes); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents with the proviso that the sulfur-containing solvent is not dimethyl sulfoxide (e.g., carbon disulfide, tetrahydro-thiophene-1,1,-dioxide); and phosphorus-containing solvents (e.g., hexamethylphosphoric triamide).

In one embodiment, the organic solvent is a saturated aliphatic hydrocarbon (e.g., n-pentane, n-hexane, n-heptane, n-octane).

In one embodiment, the organic solvent is an aromatic hydrocarbon (e.g., benzene, toluene, xylenes).

In one embodiment, the organic solvent is an aliphatic alcohol (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol).

In one embodiment, the organic solvent is an ether with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane).

In one embodiment, the organic solvent is a ketone (e.g., acetone, methyl ethyl ketone).

In one embodiment, the organic solvent is an ester (methyl acetate, ethyl acetate).

In one embodiment, the organic solvent is a nitrogen-containing solvent (e.g., formamide, N,N-dimethylformamide, acetonitrile, N-methyl-pyrrolidone, pyridine, quinoline, nitrobenzene).

In one embodiment, the organic solvent is a sulfur-containing solvent with the proviso that the sulfur-containing solvent is not dimethyl sulfoxide (e.g., carbon disulfide tetrahydro-thiophene-1,1,-dioxide).

In one embodiment, the organic solvent is a phosphorus-containing solvent (e.g., hexamethylphosphoric triamide).

In one embodiment, the organic solvent is not petroleum ether.

In one embodiment, the organic solvent is not toluene.

In one embodiment, the organic solvent is not acetone.

In one embodiment, the organic solvent is not ethanol. In one embodiment, the agent is nicotine or NNK or a combination thereof.

Suitably, the methods discussed above comprise the additional step of contacting the cell in the cell culture device with one or more small hydrophobic molecules or organic solvents as discussed above.

Suitably, the cell culture device can include a cell contained in a cell culture medium and optionally one or more small hydrophobic molecules or organic solvents as discussed above. There is also disclosed a method for determining the effect (for example, the exposure response) of one more agents on a cell comprising: (i) contacting a cell with the cell culture device described herein—such as a cell culture plate or a multi-well cell culture plate or an insert—comprising or consisting of PEEK; (ii) exposing the cell to one or more small hydrophobic molecules or organic solvents as discussed above; and (iii) determining the effect of the agent(s) on the cell.

There is also disclosed a method for determining the effect (for example, the exposure response) of one more agents on a cell comprising: (i) contacting a cell with the cell culture device described herein—such as a cell culture plate or a multi-well cell culture plate or an insert—manufactured (exclusively) from PEEK; (ii) exposing the cell to one or more small hydrophobic molecules or organic solvents as discussed above; and (iii) determining the effect of the small hydrophobic molecules or organic solvents as discussed above on the cell.

There is also disclosed a method for reducing or inhibiting the absorbance of one or more small hydrophobic molecules or organic solvents as discussed above into the cell culture device described herein comprising contacting the agent with a cell culture device comprising or consisting of PEEK. The invention is further described in the Example below, which is provided to describe the invention in further detail.

This example, which sets forth a preferred mode presently contemplated for carrying out the invention, is intended to illustrate and not to limit the invention.

EXAMPLES

Example 1

Figure 11:
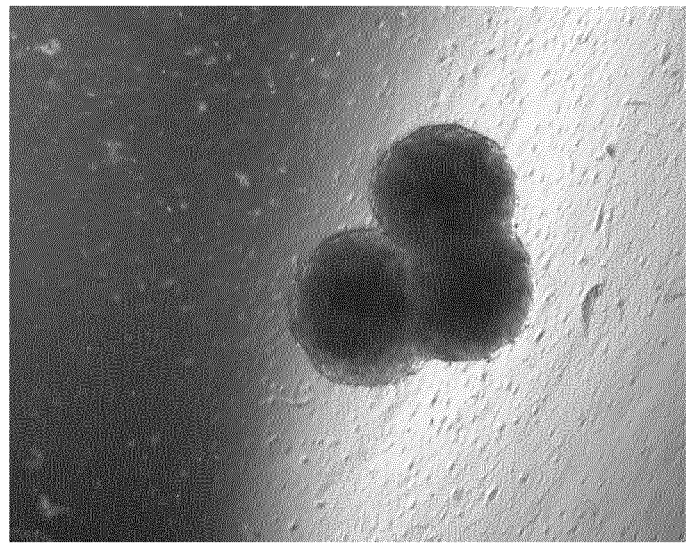
FIG. 11(a) shows agglomerated spheroids.
FIG. 11(b) shows non-agglomerated spheroids in individualised form obtained according to the present disclosure.
Figure 11:
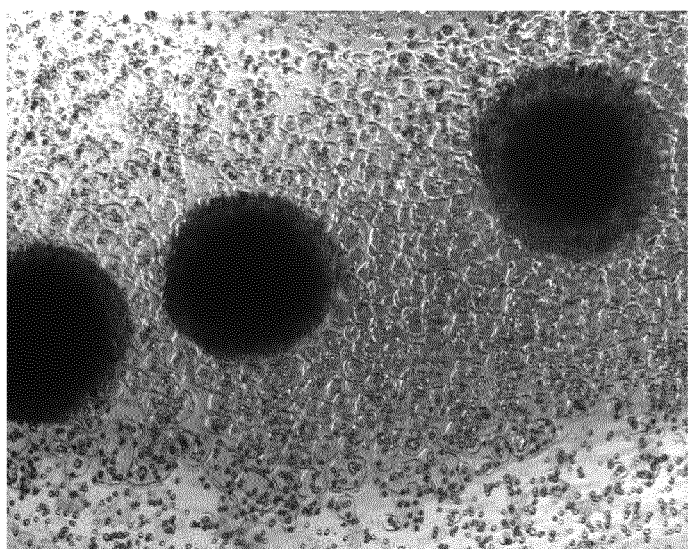

To avoid the agglomeration of spheroids, the well designed for the liver spheroids was adapted to contain concentric grooves on the bottom of the well. The purpose of these grooves is to create a spatial separation between the tissues to prevent them from agglomerating or fusing together. To demonstrate the function of the grooves, 40 spheroids, each composed of about 25,000 cells, were placed either in a well with the grooves or in a well with a flat surface (ie. without grooves). After 5 days, spheroids present in the well with a flat surface were starting to agglomerate together (see FIG. 11A) forming aggregates. This was not observed in the well with the grooves (see FIG. 11B). The tissue shown in FIG. 11A (3 spheroids agglomerated or fused to form a single unit) could not be used for further experiments normally performed on the spheroids—such as measuring the ATP content since the agglomeration or fusion of several spheroids adversely affects the result obtained. The tissue cultured in FIG. 11B did not agglomerate or fuse and was used for further experiments.

Example 2

Various materials used to manufacture a cell culture device have been tested. One material used for the cell culture device, PEEK, is a strong plastic polymer that is resistant to wear. PEEK is advantageous in drug testing because it is non-absorbent as opposed to, for example, the commonly used poly(dimethylsiloxane) (PDMS), which is known to retain small hydrophobic molecules, such as nicotine. PEEK has been found not to retain nicotine or NNK, another small hydrophobic molecule. Therefore, the cell culture device is suitable for the testing of drug effects on the tissues housed within the cell culture device without risk of the drug concentration (or concentration of its metabolites) being altered by the material.

Biocompatibility of the PEEK cell culture device is tested with organotypic lung and liver models.

The lung model is composed of normal human bronchial epithelial (NHBE) cells seeded on a Transwell™ insert and further cultured at the air-liquid interface to ensure differentiation of the cells into goblet and ciliated cells. Using these tissues we can demonstrate that the lung tissues can survive for 4 weeks in a PEEK plate as demonstrated by:

The presence of ciliated and goblet cells in a similar proportion to that observed in control tissues (from the same batch) maintained in 24-well polycarbonate plates for the same duration.

An intact morphology. Histological analysis of tissues maintained in the plate and those maintained in the 24-well plate for 4 weeks confirmed similar morphologies. Epithelial thickness, differentiation state and proportion of goblet, basal and ciliated cells were similar between tissues maintained under these two conditions.

Stable ATP content. ATP is used for several processes in cells, and all metabolically active cells contain ATP, which makes ATP content measurements a good indicator of tissue health. Tissues maintained in the plate for 4 weeks had a similar ATP content (ca. 10% less ATP) compared with control tissues.

Active cilia beating. Ciliated cells were not only still present in the same proportion as in control tissues, they were also still actively beating with a frequency similar to the one observed in control tissues.

A higher transepithelial electrical resistance (TEER). TEER measures the integrity of tight junctions in epithelial tissues and is therefore a strong indicator of barrier integrity. Tissues maintained in the PEEK plate had 50% higher TEER values than control tissues.

A retained metabolic capacity. Cytochrome P450 (CYP) inducibility, a hallmark of metabolic capacity, was tested by exposing the tissues to specific CYP enzyme inducers. After 48-hour induction, CYP1A1 activity was found to be increased 100-fold, demonstrating the retained metabolic capacity of tissues kept in the plate.

As a liver model, spheroids composed of HepaRG™ cells are used. The first results obtained with these liver spheroids following 4 weeks of culture in the PEEK plate demonstrate:

A stable secretion of albumin into the circulating medium. Albumin is a key marker of hepatic function. Within the PEEK plate albumin secretion was found to be stable for 4 weeks, with a similar albumin concentration as observed with control tissues.

Figure 12:
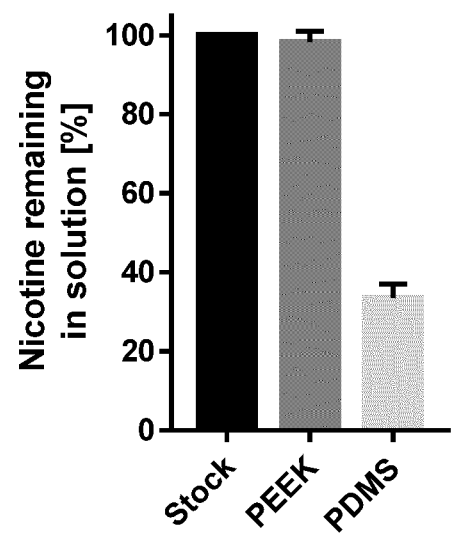
FIG. 12 shows a graph comparing the amount of nicotine remaining in a PEEK plate and a PDMS plate after 8 hours incubation at 4° C.

A retained metabolic capacity. Cytochrome P450 (CYP) inducibility, a hallmark of metabolic capacity, was tested by exposing the tissues to specific CYP enzyme inducers. After 48-hours induction, CYP1A1 activity was found to be similar to the activity observed in control tissues PEEK has the advantage of not being absorbent towards small molecules. The absorbance of PEEK towards nicotine and NNK was tested, and it was found that molecules were not trapped by the material. This is important since materials used for commercially available plates such as PDMS are known to trap small hydrophobic molecules. FIG. 12 shows the results of a graph comparing the amount of nicotine remaining in a PEEK plate and a PDMS plate after 8 hours incubation at 4° C. As can be seen, about 100% of the nicotine remained in the PEEK plate compared to about 35% in the PDMS plate. Thus, materials used for commercially available plates using PDMS will trap small hydrophobic molecules.

Example 3

HepaRG® cells are provided in cryopreserved vials containing about 10 million cells. The first step to prepare spheroids is to thaw the cryopreserved vials and to seed the cells (about 1000 to 50,000 cells per well) in each well of a multi-well plate. In this experiment, the wells of the plate are covered with an ultra-low attachment coating and the wells have a U-shaped bottom to ensure that the cells seeded in a single well do not attach to the walls. The cells are allowed to agglomerate at the bottom of the well. After about 3 days they will form a single spheroid or multiple spheroids in each well of the multi-well plate, depending on the choice of well that is used.

The cell culture chamber of the cell culture device into which the liver spheroids are placed has the discontinuous surface described herein which, in this example, is coated. Each spheroid is transferred independently from the multi-well plate to the cell culture chamber. Around 40 to 100 spheroids are transferred per compartment. The cell culture device is connected to a pump which creates a medium flow. The spheroids can remain for between 1 to 28 days in the cell culture device before we use them for other experiments.

Further aspects of the present disclosure are set forth in the following numbered paragraphs:

1. A cell culture device for culturing cells, comprising:
    a cell culture chamber comprising a base and side walls extending from the base to enclose a volume of the cell culture chamber,
    an inlet in the base or side walls of the cell culture chamber adapted for fluid communication into the chamber; and
    an outlet in the base or side walls of the cell culture chamber adapted for fluid communication out of the chamber;
    wherein the base of the cell culture chamber comprises a discontinuous surface adapted to reduce or prevent the agglomeration of spheroids.
2. The cell culture device according to paragraph 1, wherein the base of the cell culture chamber is substantially circular in shape, suitably, wherein the diameter of the base is between about 6 mm±5% and about 22 mm±5%, suitably, wherein the diameter of the base is about 6 mm±5%, about 11 mm±5%, about 16 mm±5% or about 22 mm±5%.
3. The cell culture device according to paragraph 1 or paragraph 2, wherein the discontinuous surface comprises a plurality of grooves in which the depth and width of the grooves corresponds to the largest diameter±10% of a spheroid.
4. The cell culture device according to paragraph 3, wherein the depth and width of the plurality of grooves is between about 200 to about 1000 μm, suitably, between about 600 to about 1000 μm.
5. The cell culture device according to paragraph 3 or paragraph 4, wherein the grooves form a plurality of concentric rings on the base of the cell culture chamber.
6. The cell culture device according to paragraph 1 or paragraph 2, wherein the discontinuous surface comprises a plurality of holes having a closed bottom and an open top, the size of the holes corresponding in depth and width to be about 10% greater than the largest diameter of a spheroid.
7. The cell culture device according to any of the preceding paragraphs, wherein the cell culture chamber comprises cell culture medium for culturing spheroids.
8. The cell culture device according to any of the preceding paragraphs, wherein the cell culture chamber comprises individual spheroids trapped in the discontinuous surface of the cell culture chamber.
9. The cell culture device according to paragraph 8, wherein the spheroids are lung spheroids.
10. The cell culture device according to any of the preceding paragraphs, wherein the flow of fluid from the inlet to the outlet of the cell culture chamber, when fluid is present therein, is between about 10 to about 1000 μL/min, suitably, about 1 to about 500 μL/min, suitably, about 40 μL/min.
11. The cell culture device according to paragraph 10, wherein the shear stress in the cell culture chamber is less than 0.1 dynes/cm$^2$.
12. The cell culture device according to any of the preceding paragraphs, wherein the cell culture device is a multi-well plate and each chamber of the multi-well plate is a well, said multi-well plate comprising at least two wells.
13. The cell culture device according to any of the preceding paragraphs, wherein the base of at least one of the chambers comprises a flat surface that is devoid of discontinuities.

14. The cell culture device according to paragraph 13, wherein the at least one chamber comprises an insert positioned above the base of the chamber, suitably, wherein the insert is located on top of a permeable membrane located inside the chamber to form a surface that is capable of culturing a cell at an air/liquid interface.

15. The cell culture device according to paragraph 13 or 14, wherein the depth of the at least one chamber comprising the flat surface that is devoid of discontinuities is different to the depth of the at least one chamber comprising the discontinuous surface, suitably, wherein the depth of the at least one chamber comprising the flat surface that is devoid of discontinuities is less than the depth of the at least one chamber comprising the discontinuous surface.

16. The cell culture device according to any of paragraphs 13 to 15, wherein the cell culture chamber comprises cell culture medium for culturing a cell at an air-liquid interface.

17. The cell culture device according to paragraph 16, wherein the cell culture chamber comprises cells positioned on the permeable membrane, said cells being capable of growing at an air-liquid interface.

18. The cell culture device according to paragraph 17, wherein the cells are lung cells.

19. The cell culture device according to any of paragraphs 12 to 18, wherein the at least two wells are in fluid communication with each other.

20. A method of culturing a cell comprising:
(i) providing the cell culture device according to any of paragraphs 1 to 19;
(ii) contacting the cell culture device with cell culture medium and at least one cell type; and
(iii) culturing the cell.

21. A method of preparing a cell culture device for culturing spheroids, comprising:
(i) providing a cell culture chamber comprising: (a) a base and side walls extending from the base to enclose a volume of the cell culture chamber; (b) an inlet in the base or side walls of the cell culture chamber adapted for fluid communication into the chamber; and (c) an outlet in the base or side walls of the cell culture chamber adapted for fluid communication out of the chamber; and
(ii) adding a discontinuous surface to the base of the cell culture chamber, wherein the discontinuous surface is adapted to reduce or prevent the agglomeration of spheroids.

22. The method according to paragraph 21, wherein the discontinuous surface is as defined in any of paragraphs 3 to 6.

23. The method according to paragraph 21 or paragraph 22, wherein the discontinuous surface is provided to the base using computer numerical control machining or injection moulding.

24. A cell culture chamber comprising a base having a discontinuous surface, wherein the discontinuous surface comprises individualised single spheroids trapped therein.

25. The cell culture chamber according to paragraph 24, wherein the discontinuous surface is as defined in any of paragraphs 3 to 6.

26. A cell culture device comprising the cell culture chamber according to paragraph 24 or paragraph 25.

27. The cell culture device according to any of paragraphs 1 to 19 and 26, wherein the device is a multi-well plate.

28. The cell culture chamber according to paragraph 24 or paragraph 25, wherein the chamber is a well.

29. Use of the cell culture device according to any of paragraphs 1 to 19, 26 and 27 or the cell culture chamber according to any of paragraphs 24, 25 or 28 for culturing a spheroid or for maintaining spheroids in an individualised single form.

30. A culture of spheroids, wherein the spheroids are in the form of individualised single spheroids after 5 hours or 5 days of culture.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in engineering, cellular biology and molecular biology or related fields are intended to be within the scope of the following claims.

The invention claimed is:

1. A method of reducing or preventing the agglomeration of spheroids comprising:
(i) providing one or more individual spheroids, wherein the spheroid is a ball or aggregation of cells in three dimensions; and
(ii) transferring the individual spheroid(s) into a cell culture chamber of a cell culture device comprising:
the cell culture chamber, wherein the cell culture chamber comprises a base and side walls extending from the base to enclose a volume of the cell culture chamber;
an inlet in the base or side walls of the cell culture chamber adapted for fluid communication into the chamber; and
an outlet in the base or side walls of the cell culture chamber adapted for fluid communication out of the chamber;
wherein the base of the cell culture chamber comprises a discontinuous surface configured to trap one or more individual spheroids to reduce or prevent the agglomeration thereof.

2. The method according to claim 1, wherein a known number of individual spheroids are transferred in step (ii) and a known number of individual spheroids are trapped.

3. The method according to claim 1, wherein the discontinuous surface comprises a plurality of grooves in which the depth and width of the grooves is between about 200 to about 1000 µm.

4. The method according to claim 3, wherein the grooves form a plurality of concentric rings on the base of the cell culture chamber.

5. The method according to claim 1, wherein the discontinuous surface comprises a plurality of holes having a closed bottom and an open top, the size of the holes corresponding in depth and width to be about 10% greater than the largest diameter of a spheroid.

6. The method according to claim 1, wherein the cell culture chamber is manufactured from PEEK.

7. The method according to claim 1, wherein the cell culture chamber is coated.

8. The method according to claim 1, wherein between about 40 to about 100 spheroids are transferred to the cell culture chamber of the cell culture device.

9. The method according to claim 1, wherein a medium flow is applied to the cell culture chamber of the cell culture device.

10. The method according to claim 3, wherein the depth and width of the grooves is between about 200 to about 600 µm.

11. The method according to claim 7, wherein the coating is a coating of poly (p-xylylene) polymer.

12. The method according to claim 9, wherein the flow rate is between about 10 to about 1000 µL/min.

* * * * *